US008882676B2

(12) United States Patent
Hughes

(10) Patent No.: US 8,882,676 B2
(45) Date of Patent: Nov. 11, 2014

(54) METHOD AND DEVICE FOR MEASURING THE RSA COMPONENT FROM HEART RATE DATA

(75) Inventor: Darran John Hughes, Dublin (IE)

(73) Assignee: Zinc Software Ltd., Dublin (IE)

( * ) Notice: Subject to any disclaimer, the term of this patent is extended or adjusted under 35 U.S.C. 154(b) by 310 days.

(21) Appl. No.: 13/150,490

(22) Filed: Jun. 1, 2011

(65) Prior Publication Data

US 2011/0301477 A1 Dec. 8, 2011

Related U.S. Application Data

(60) Provisional application No. 61/351,007, filed on Jun. 3, 2010.

(51) Int. Cl.
*A61B 5/02* (2006.01)
*A61B 5/0205* (2006.01)
*A61B 5/024* (2006.01)
*A61B 5/00* (2006.01)

(52) U.S. Cl.
CPC ........... *A61B 5/0205* (2013.01); *A61B 5/02405* (2013.01); *A61B 5/4035* (2013.01); *A61B 5/486* (2013.01)
USPC ......................................................... 600/501

(58) Field of Classification Search
CPC .... A61B 5/0205; A61B 5/486; A61B 5/4035; A61B 5/02405
USPC .................................................. 600/529, 543
See application file for complete search history.

(56) References Cited

U.S. PATENT DOCUMENTS

| 6,305,943 | B1 | 10/2001 | Pougatchev et al. |
| 2006/0155167 | A1 | 7/2006 | Elliott |
| 2007/0299354 | A1 | 12/2007 | Striepe et al. |

FOREIGN PATENT DOCUMENTS

| EP | 2392256 A1 | | 7/2011 |
| GB | WO2009016334 | * | 2/2009 |
| WO | WO2005044092 A2 | | 5/2005 |
| WO | WO 2009/016334 A1 | * | 2/2009 |
| WO | WO2009136307 A1 | | 11/2009 |

OTHER PUBLICATIONS

Smith, Steven W. "The Scientist and Engineer's Guide to Digital Signal Processing", Chapter 33, © 1997-1998.*

(Continued)

*Primary Examiner* — Patricia Mallari
*Assistant Examiner* — Michael J Burrage
(74) *Attorney, Agent, or Firm* — Soquel Group LLC

(57) ABSTRACT

A device for providing biofeedback information to a subject, including a receiver for receiving heart rate data from a sensor, said heart rate data corresponding to a human subject, a storage device for storing a time series of the received heart rate data, a display, and a processor that is programmed to enable access to the storage device and to perform actions including estimating an RSA strength of the subject's heart from the time series of the received heart rate data, calculating an accumulated RSA strength from a designated starting time until the present time, determining a motion by a virtual agent based on the accumulated RSA strength at the present time, said virtual agent being a graphical object or character that represents the subject, and displaying the motion of the virtual agent determined by said determining on the display.

7 Claims, 10 Drawing Sheets

(56) References Cited

OTHER PUBLICATIONS

Chon, K.H., et al., "Estimation of Respiratory Rate From Photoplethysmogram Data Using Timed Frequency Spectral Estimation", (Aug. 2009) IEEE Transactions on Biomed. Eng., IEEE Svc. Ctr, Piscataway, NJ, USA, vol. 56, No. 8, (ISSN: 0018-9294), pp. 2054-2063.

European Search Report, The Hague (Sep. 2011), EP11168697, pp. 24-27.

* cited by examiner

FIGURES 7A-D

METHOD AND DEVICE FOR MEASURING THE RSA COMPONENT FROM HEART RATE DATA

REFERENCE TO RELATED APPLICATIONS

This application claims benefit of U.S. Provisional Application No. 61/351,007, entitled Method For Measuring RSA Component From Heart Rate Data, filed on Jun. 3, 2010 by inventor Darran John Hughes.

FIELD OF THE INVENTION

The present invention relates to a method for measuring the respiratory sinus arrhythmia (RSA) component of heart rate variability (HRV) and device utilizing this method. The invention further relates to biofeedback, or anxiety management, applications based on the method and system for measuring the RSA component of heart rate variability.

BACKGROUND

The history of heart rate analysis can be traced back to the turn of the century when correlations between heart rate variations and the underlying physiological and psychological state of a human subject began to be investigated with several early pioneers such as Willem Einthoven.

The arrival of computerized methodologies in the 1950s and 60s greatly increased the ability to identify underlying patterns and led to an increased understanding of the heart's control systems.

The variations and patterns of the heart rate over time can be used to infer actions caused by the two key control subsystems of the autonomic nervous system (ANS): the sympathetic subsystem and the parasympathetic subsystem. Respiratory Sinus Arrhythmia (RSA) is one such variation of heart rate that occurs through the influence of breathing on the balance of sympathetic and parasympathetic control over the heart muscle. This is due to a reducing of effect of the parasympathetic during inhalation via baroreflex action (reduced blood pressure) which causes the heart rate to increase and a reversal of this effect during exhalation where heart rate is seen to decrease. FIG. 1 illustrates the type of heart rate pattern seen when the RSA component is strong. This effect is most noticeable in rest conditions where the balance is shifted towards parasympathetic control and so these baroreflex effects become key modulators within the system. During periods where the sympathetic system dominates, the RSA component in the heart rate data can be negligible, as illustrated in FIG. 2.

The respiratory sinus arrhythmia (RSA) pattern was first noticed within cardiograms in the 1950s and was being used by clinicians as a test of autonomic balance by the 1970's. Wheeler and Watkins, in 1973, document a method of measuring a subject's RSA by comparing the highest and lowest heart rate achieved during a 5 minute period while breathing deeply at a rate of 6 breaths per minute.

In the 1980s a measure of RSA was first utilized within a biofeedback framework by Alexander Smetankin with the invention of his cardiosignalizer, a device for providing audio and visual feedback of the RSA component of the heart rate signal using a methodology similar to that described by Wheeler and Watkins.

As RSA strength is a key sign of autonomic balance it can be used within biofeedback applications to help achieve deeper levels of relaxation. In practice this means linking deep breathing exercises, which induce stronger RSA heart patterns, with visual or audio feedback of RSA strength to train users in breathing based relaxation techniques. The state reached via these exercises is sometime called "cardiac coherence" and is indicated by a high RSA component of the heart signal.

Biofeedback is the process of presenting back to a person a metric of some aspect of their physical state that they are not usually conscious of so that they can be trained to develop stronger conscious control over this physical property. A classic example of this would be a person with balance control problems standing on a balance board which measures their center of gravity and changing the volume or frequency of an audio tone depending on how far their center of gravity moves from some target position. In this way a person can learn to adapt their muscle control based on this feedback and so achieve better balance. When administered therapeutically, biofeedback is typically administered in a series of sessions by a trained technician using a biofeedback device to a subject.

RSA based biofeedback has been shown to be useful in controlling anxiety and stress and clinical trials have shown its efficacy in reducing high blood pressure. Instantaneous RSA can be used as a biofeedback parameter to modulate audiovisual representations to a subject or user, giving him/her an indication of how a paced breathing exercise is affecting his/her heart patterns. Simple examples of this include modulating the screen color displayed to the user or modulating the frequency of an audio tone played to the subject.

A general measure of RSA strength, $S'(t)$, can be defined as a maximum of the cross correlation function of the heart rate signal $H(t)$ and a function of breathing rate $B(t)$ calculated over a synchronous window of time as in Equation 1 below:

$$S'(t) = \max(H(t) * B(t)) \qquad (1)$$

where * represents the cross-correlation function applied to the two signals over the same time interval and max represents the maximum value function.

As breathing rate can be less convenient to measure than heart rate, the measure $S'(t)$ is often estimated with $B(t)$, defined a priori as a sinusoidal function with amplitude 1.0 and a target breathing frequency at which the user is instructed to breath at, usually defined in the range 0.05 to 0.2 Hertz. This allows $S'(t)$ to be estimated without direct measure of breath air flow or lung volume.

Several sensor technologies can be utilized to transduce heart activity into electrical signals available for processing and RSA feature analysis. These sensors include microphone (audio heart signals), pressure sensors (pulse pressure), electrocardiogram (ECG), photoplethysmography (PPG), as well as non-contact sensors that utilize RF technologies.

In recent years, consumer PPG products have appeared on the market. A coincident trend is the adoption of mobile devices with graphical user interfaces, audiovisual and wireless capabilities. As mobile devices become increasingly ubiquitous, a wireless PPG or ECG sensor product that communicates sensor data to a mobile device that performs post-processing is desirable since it can reduce cost by working in a subject's existing mobile device and it can be very convenient to use.

In such a system where an external computing device (such as mobile phone) performs the digital signal processing required for RSA feature extraction there is a need for a robust and highly scalable method that can achieve this goal within the context of widely varying computational abilities of mobile devices on the market.

However, current methods for determining RSA based on cross correlation or power spectrum analysis are often too computationally demanding to run in real time on many mobile devices. Thus there is a need in the market for a method of extracting the RSA component of a heart rate signal that can be used across a wide spectrum of computing devices, including mobile devices that may be resource constrained.

SUMMARY OF THE INVENTION

The present invention discloses a RSA biofeedback application that guides user on techniques of paced breathing to achieve a state of heart coherence. The present invention further discloses a points based system that rewards a subject by assigning points when goals are met.

The subject invention specifies a method that efficiently estimates a metric of the RSA component of a human subject's heart rate from a data stream of raw heart beat intervals.

The RSA strength estimation method segments a digital heart rate signal into overlapping windowed segments of data and calculates a best fit all pole linear filter (autoregressive model) for each window of heart beat intervals. A single pole within a target sector of the complex plane is identified as the RSA pole and an estimate of RSA strength is calculated based on the following equation, $$S_{RSA} = kE_W\left(\frac{1}{1-|P_{RSA}|}\right) \quad (2)$$

where $|P_{RSA}|$ is the modulus of the identified RSA pole, $E_W$ the total window energy and k is a proportionality constant.

A key advantage in this method is by scaling the degree of the filter model it allows the method to scale its processing efficiency. This is especially useful when the processing is being offloaded to a computing device, such as a mobile device, with computational capabilities that may have inadequate computational capability to perform complex fast fourier transform (FFT) processes in real time. The autoregressive methodology also allows for higher resolution identification of RSA strength using shorter data segments. Shorter data segments may be preferred for certain biofeedback applications, as shorter data windows yield faster updates of a subject's physiological state.

In a preferred embodiment, the current invention incorporates the calculation of an expected value of the heartbeat interval time series. As the all pole filter can be utilized as a short term predictor of signal variation. These predicted values can be used to perform error correction on the raw beat-to-beat data stream. As heart rate data can be corrupted by external noise and internal physiological effects (such as ectopic beats) it is often necessary to preprocess a time series to identify possible corrupt heart beat samples and replace with samples that would be expected given the previously sample values. Using the all pole filter method these replacement values are generated automatically and so reduce the overhead required to preprocess and error correct the data.

In one embodiment, the present invention calculates the argument (or phase) of RSA pole ($P_{RSA}$) and uses this value to estimate the breathing rate of a subject. RSA strength peaks at a specific breathing rate which can be different for each person. This feature allows this breathing rate to be stored and utilized by the user when no biosensor equipment is available (such as using a timer or clock to sync breathing).

The subject invention further provides a device for providing biofeedback information to a subject, including a receiver for receiving heart rate data from a sensor, said heart rate data corresponding to a human subject, a storage device for storing a time series of the received heart rate data, a display, and a processor that is programmed to enable access to the storage device and to perform actions including estimating an RSA strength of the subject's heart from the time series of the received heart rate data, calculating an accumulated RSA strength from a designated starting time until the present time, determining a motion by a virtual agent based on the accumulated RSA strength at the present time, said virtual agent being a graphical object or character that represents the subject, and displaying the motion of the virtual agent determined by said determining on the display.

BRIEF DESCRIPTION OF THE DRAWINGS

These embodiments and other aspects of this invention will be readily apparent from the detailed description below and the appended drawings, which are meant to illustrate and not to limit the invention, and in which.

DETAILED DESCRIPTION

The invention will be more completely understood through the following detailed description, which should be read in conjunction with the attached drawings. Detailed embodiments of the invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the invention in virtually any appropriately detailed embodiment.

Figure 1:
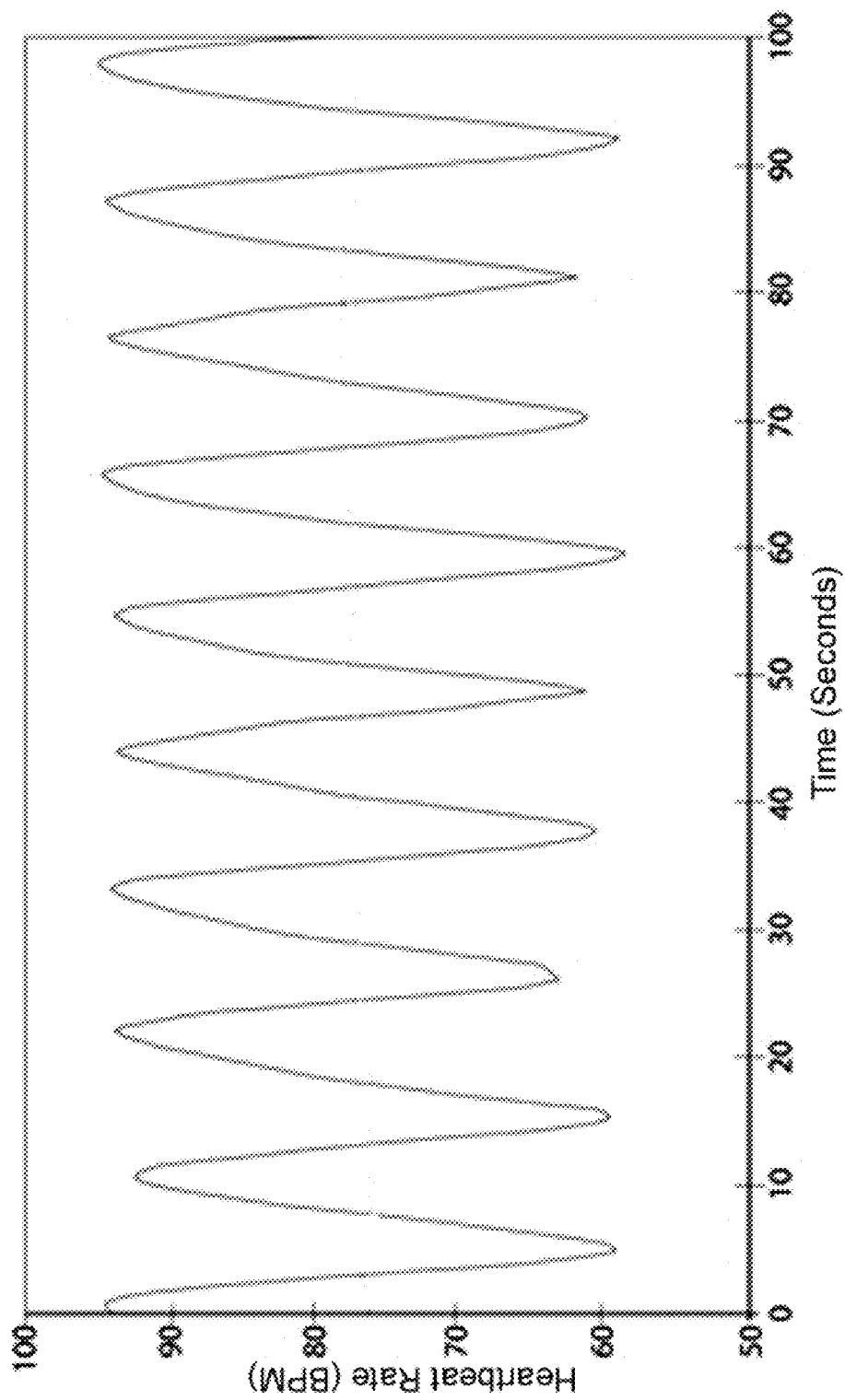
FIG. 1 illustrates an exemplary variation of a subject's heart rate over time when the RSA component is strong.
Figure 2:
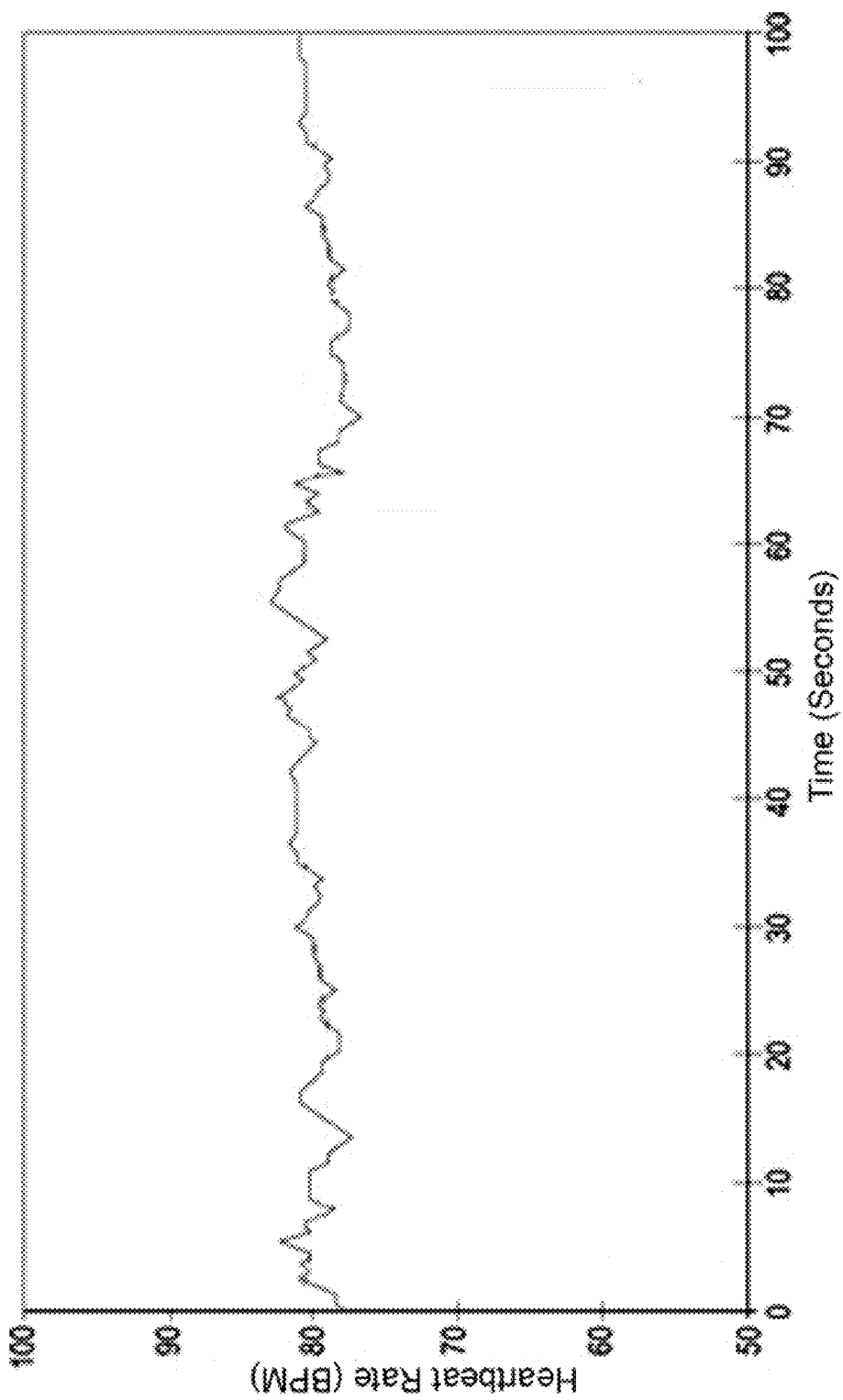
FIG. 2 illustrates an exemplary variation of a subject's heart rate over time when the RSA component is weak.
Figure 3:
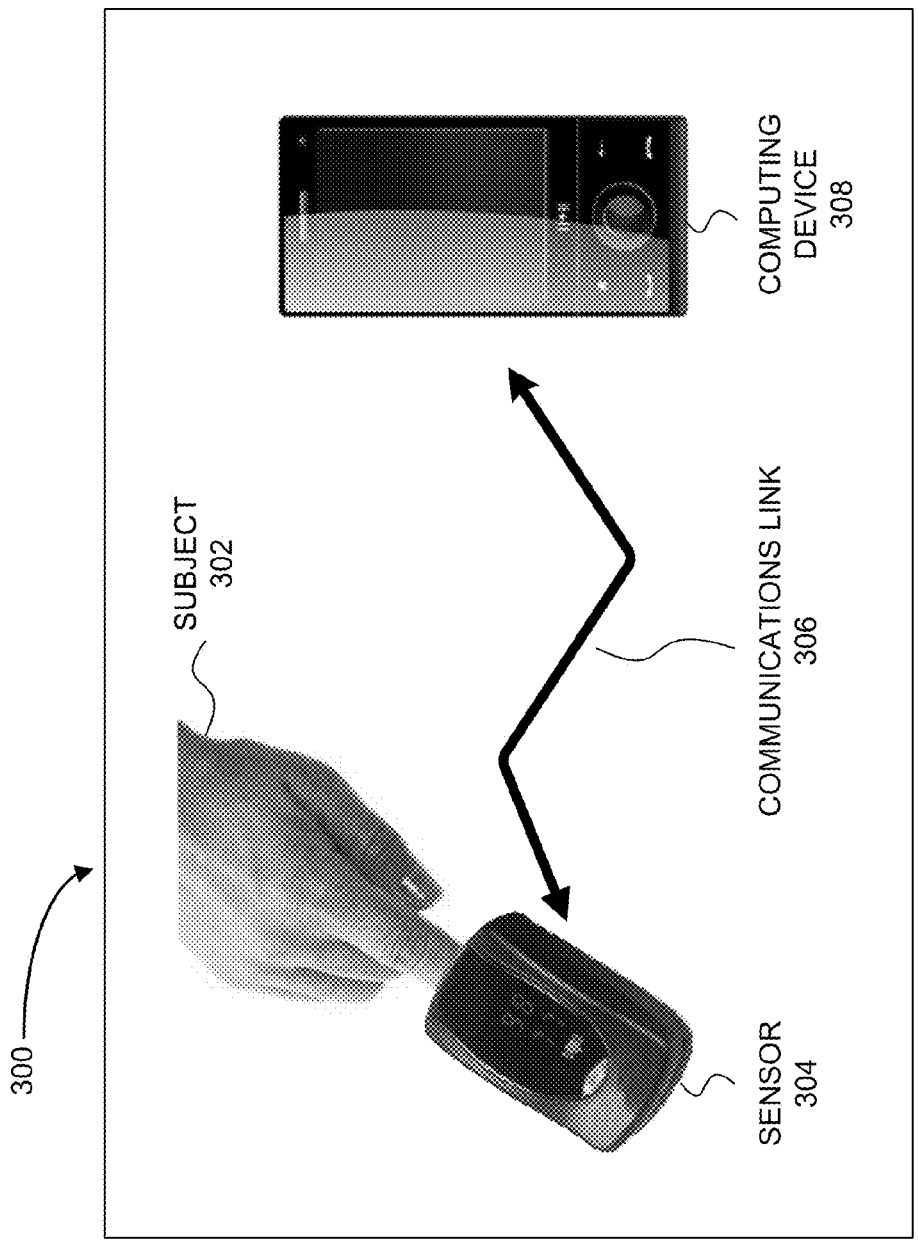
FIG. 3 is a system diagram of an exemplary embodiment of the subject invention.

FIG. 3 is a system diagram of an exemplary embodiment 300 of the subject invention. A sensor 304 takes heart rate measurements of a human subject 302. Most preferably sensor 304 communicates the raw heart rate sensor data across a communications link 306 to a computing device 308 which analyzes the heart rate data and extracts a RSA metric. In a preferred embodiment communications link 306 is a near field communications link, e.g. by using BLUETOOTH communications. However, communication link 306 is not limited to near field communications, for example a wide area network such as the Internet, wireless communications, local area communications networks. Generally, communications link 306 may be provided by any type of communications links or networks that support data communications. In a preferred embodiment the RSA metric is used by a biometric application, an application running in computing device 308 that provides dynamic biofeedback to subject 302 based on the processed sensor data. While sensor 304 is depicted as a commercial oximeter, the invention is not so limited and other heart rate sensors may be used. In addition, while computing device 308 is depicted as a smart phone, any type of computing device including inter alia mobile phones, laptop computers, pad computers, game consoles, set top boxes such as those used in cable TV systems, and personal computers may be used. Computing device 308 at a minimum possesses a processor, data storage for storing program code and data, communications ability for communicating with sensor 304 and a display for displaying graphical results by a biometric application.

Method for Calculating RSA Strength from Heart Rate Data

Figure 4:
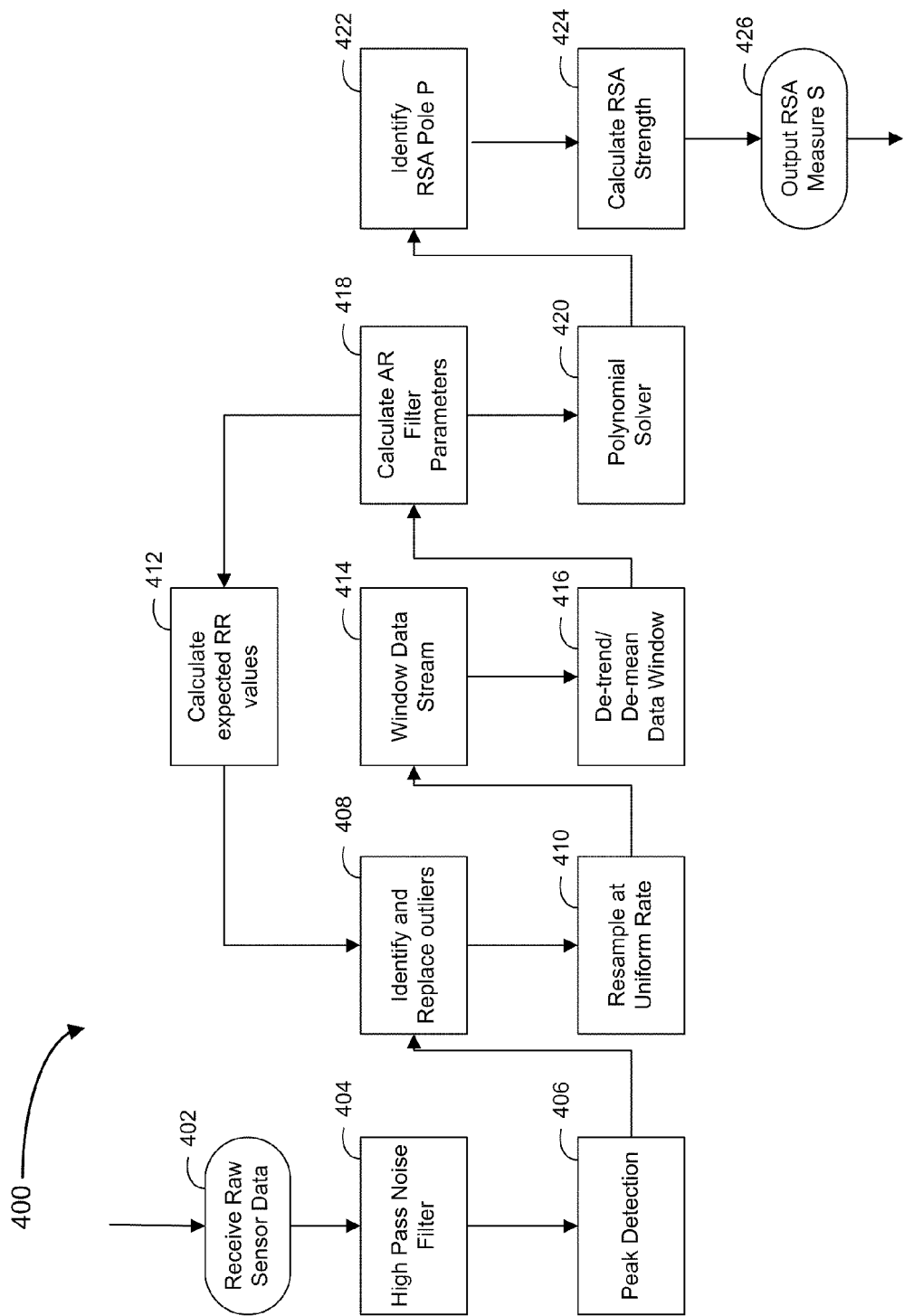
FIG. 4 is a flow diagram of a preferred method for extracting an RSA metric from raw heart rate sensor data.

FIG. 4 is a flow diagram of a preferred method 400 for extracting an RSA metric from raw heart rate sensor data. In method 400 raw sensor data feed 402 comes from a heart rate measurement device, i.e. an embodiment of sensor 304. Examples of such heart rate measure measurement devices include a photoplethysmograph (PPG) which is an optically obtained plethysmograph, a volumetric measurement of an organ, and an electrocardiographic (ECG) device. Generally, method 400 works with any data signal from a sensor or transducer that measures or provides electrical signals concerning an aspect of the human heart beat. In a successfully tested prototype, sensor 304 is implemented as a Nonin 9560 oximeter which connects using a BLUETOOTH near field communications link to a Nokia N97 mobile device. The Nonin BLUETOOTH oximeter data stream is accessed using the JSR82 JAVA BLUETOOTH software module available on the Nokia N97 and PPG heart rate sensor data, represented as 16 bit unsigned data, is transmitted to the Nokia N97 at a rate of 75 samples per second.

The raw sampled heartbeat sensor data stream is converted into a time series of inter beat interval time, referred to herein as IBI data, by first low pass filtering to reduce noise at step 404 and then, at step 406 a peak detection algorithm determines the local maximum peak for each heartbeat and outputs the time interval between peaks. The incoming raw data is filtered using a low pass filter and trends are removed by applying a moving average filter. In one embodiment, a Chebyshev filter of order 4 with a cutoff frequency of 4.0 Hz is used for this purpose.

This allows a zero mean signal with reduced noise to be passed into a threshold based peak detection algorithm at step 406. Peaks are detected by comparing all points with a first differential equal to zero, which indicates a potential peak, and finding the maximum within the positive range of each heartbeat cycle. This is a method known in the art of digital signal processing (DSP) for performing robust peak detection on biological signals.

At step 408 the IBI data, with units in seconds, is then analyzed in order to identify and replace outliers where an outlier is a value that lies outside the current normal variation and trend within the IBI data stream. Outliers can occur due to measurement noise, errors within the peak detection algorithm and also physiological reasons such as ectopic heart beats that produce either very short or very long heart beats. Ectopic beats occur in normal healthy subjects but very high ratio of these beats can be indications of heart disease. Outlier removal is achieved here by calculating an expected value for each heartbeat. A first pass to process outliers is performed using a simple moving average filter of the IBI data to calculate a mean expected value and then by defining an outlier as values outside a range around this expected value as shown below:

$$I_{outlier} < 0.7 * I_{expected} \text{ or } I_{outlier} > 1.4 * I_{expected} \quad (3)$$

Outliers are then replaced by the expected value in the IBI stream to create an error free signal for later processing.

At step 412 the expected IBI value is calculated using the AR filter model that is determined in step 418. Step 418 uses a method known in speech signal processing as Linear Predictive Coding (LPC); it gives a robust measure of the expected value in a stable and quasi stable time series. The AR model calculation is passed back from step 418. The AR model is applied to the previous n IBI values, where n is the order of the model, to calculate an estimate of the next IBI value. An AR model filter order of between 4 and 15 is used. As step 418 occurs after step 412 the values the AR model values will correspond to the previous window of IBI data. This is valid based on the presumption that the IBI signal is quasi stationary and that new data windows are taken at relatively short enough intervals. This presumption is valid for a window overlap of 5 seconds or less.

Once outliers are removed, at step 410 the IBI data stream is resampled at a uniform rate. This is required as sampling of the raw data has taken place at each peak in the raw data stream and these peaks are not uniformly spaced in time. To utilize linear system analysis the data must be provided at a uniform rate and therefore must be processed to achieve this before later processing can be applied. Uniform sampling is achieved by taking interpolated points of the IBI data at evenly spaced points. Cubic spline interpolation is applied to the non-uniform IBI data and resampled points are determined at 0.25s (4 Hz) intervals.

At step 414 the uniform IBI data stream is windowed into segments of data of length n, each window overlapping with previous window by m samples. A preferred value for n is 128 and for m is 32. Windowing refers to applying a function that is zero-valued outside a specified interval. A Hamming window function also applied to the window data to reduce distortion of the AR parameters due to the windowing process.

At step 416 the windowed data is then de-meaned, which removes the DC offset of the data, and de-trended, which removes any underlying trend from the data over the length of the data window. De-meaning and de-trending the data in a window is performed by calculating a best fit line through each data point in the window using a least mean squares algorithm and subtracting this centerline from each data point in the window.

At step 418 the data window is then processed via an autoregressive (AR) method to calculate a best fit all pole filter model for the data. AR methods can be formulated in the time domain as a linear predictive method that is used to find the best estimate of the next value in a time series based on a linear weighted sum of the preceding values, as in the following equation:

$$\hat{x}(n) = \sum_{i=1}^{p} a_i x(n-i) \quad (4)$$

Where $\hat{x}$ is the expected value and at are the predictor coefficients. This can also be seen as a transfer function in z space relating an input signal to an output signal as in the following equation:

$$H(z) = \frac{1}{\sum_{i=1}^{p} a_i z^{-i}} = \frac{z^p}{(z-z_1)(z-z_2)\ldots(z-z_p)} \quad (5)$$

In digital signal analysis, Equation 5, above, describes a transfer function in which there are p filter poles and no filter zeros. This is known as an all pole filter and the positions of the poles in the Z plane completely describe the behavior of the system. These poles can be visualized in the complex plane as a series of points within the unit circle (assuming a stable system). For real value transfer functions these poles occur in complex conjugate pairs (mirrored in the real axis). Each pole can be described in polar coordinates as having a magnitude and phase angle as shown below in Equation 6.

$$P_i = re^{i\theta} \quad (6)$$

The larger the magnitude r of a pole, $P_i$, the stronger its effect on the overall dynamics of the system. For each pole the phase angle $\theta$ is related to the frequency at which this pole exerts its effects. Each pole can be mapped to components of the data stream being modeled and the strength and frequency of this component can be tracked via the magnitude and phase of its matching pole.

There are several methods to calculate the parameters $a_1$ to $a_p$ of an all pole model from a window of input data. In a preferred embodiment the Burg method, also known as the maximum entropy method or MEM, is used. The Burg method, which is well known in the art, will estimate the parameters of an all pole filter model of order p based on window of input data. The computational efficiency of the Burg method has advantages over other methods especially for lower order systems. The Burg method also has particular advantages in analyzing short data segments (such as 30 seconds) where accurate pole estimation can be more difficult. In one embodiment, the filter order is adapted to the computational abilities of the computing device running the method. In one embodiment, used with the aforementioned N97 device, a filter order of 9 was successfully used.

The output of the Burg algorithm is the parameter set $a_1$, $a_2$, ..., $a_p$ describing the polynomial matching the transfer function, known as the Yule-Walker polynomial. At step 420, the poles of the transfer function are calculated by solving for the roots of this polynomial. Any standard root solving algorithm can be used at this step. In one embodiment, the Jenkins-Traub method, which is an efficient algorithm that gives robust results, is used.

Once the poles of the transfer function have been calculated, at step 422 the pole that relates most closely to the RSA component of the heart beat data is identified. This pole lies in a sector range constrained by the normal breathing rates of 4 to 30 breathes per second. This range can be further constrained by the fact that breathing above 20 breaths causes the sympathetic system to reduce the effect of RSA and so produce poles of lower magnitude. This relates to a frequency range from 0.07 Hz to 0.33 Hz. (It has been shown that slow controlled breathing rates around 5-7 breaths per minute causes peaks in RSA component strength). Given a sampling rate of $f_s$ this corresponds to the range of sector angles, given in Equation 7, below:

$$\frac{0.14\pi}{f_s} < \theta < \frac{0.66\pi}{f_s} \quad (7)$$

The poles within this sector are compared in terms of magnitude. A metric of the influence of each pole Pi can be defined as pole energy $E_i$ where, $$E_i = \left(\frac{1}{1-|P_i|}\right) \quad (8)$$

The pole with the greatest $E_i$ in the target sector is identified. If there are other poles in the sector of lower phase angle and have a pole energy that is greater than $0.7 \times E_i$ max then the lowest of these poles angles is identified as the RSA pole.

The total window energy $E_w$ of the de-meaned and de-trended window of IBI data, calculated via the equation below $$E_w = \sum_{i=0}^{n} (x_i)^2 \quad (9)$$

At step 424 the total strength of the RSA component is calculated using Equation 10 below:

$$S_{RSA} = kE_w E_{RSA} \quad (10)$$

Where $E_{RSA}$ is pole energy associated with the selected RSA pole $P_{RSA}$ and $E_w$ the total window energy and k is a proportionality constant used to normalize output to a target range. In one embodiment the value of k is defined as the inverse of n the number of samples in the IBI data window, which for n=128 means a value of k=0.0078. Combining Equations 9 and 10 above gives the formula below, $$S_{RSA} = kE_w\left(\frac{1}{1-|P_{RSA}|}\right) \quad (11)$$

The strength $S_{RSA}$ is a robust measure of the current RSA component of the heart rate data. In the current embodiment with RSA was strong this value of $S_{RSA}$ measure was over 1.0. $S_{RSA}$ values below 0.2 signified little or no RSA component in the IBI data window.

At step 426 $S_{RSA}$, the total strength of the RSA component is transmitted to computing device 308. In other embodiments, $S_{RSA}$ values are stored and sent upon request to computing device 308.

Figure 5:
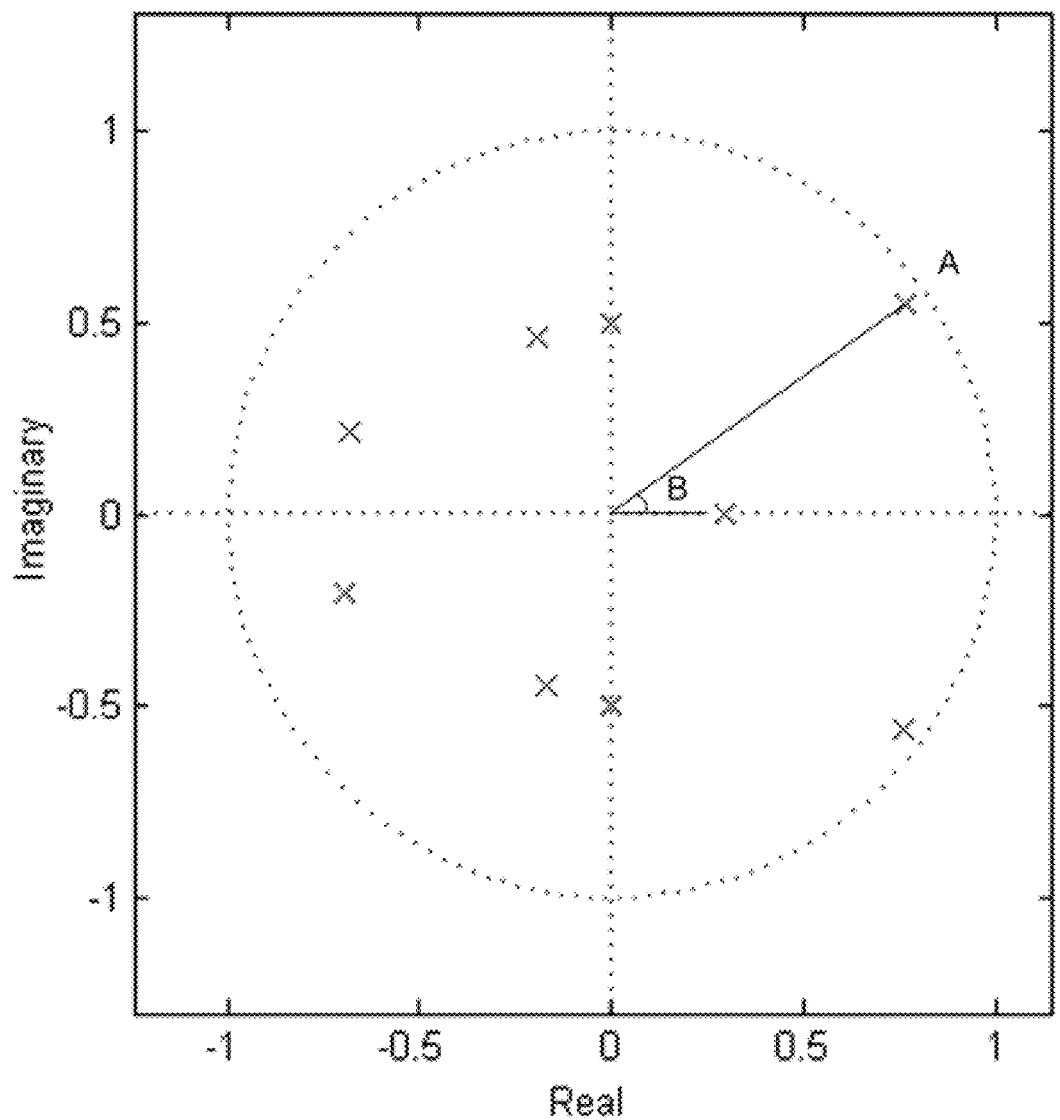
FIG. 5 depicts an Argand plot showing the pole positions of a best fit all pole filter indicating the identified RSA pole A and the phase angle of this pole B.

FIG. 5 depicts an Argand plot showing the pole positions of a best fit all pole filter indicating the identified RSA pole A and the phase angle of this pole B. The embodiment illustrated in FIG. 5 shows the calculated pole positions for one windowed segment of heart rate data using a $9^{th}$ order all pole filter model at a sampling rate of 2 Hz. Within the sector of interest one pole (marked A) has the greatest magnitude, is above the threshold strength value, and is identified as the RSA pole. The strength value $S_{RSA}$ calculated from this pole position is the output RSA measure transmitted as step 426 of FIG. 8 that is utilized in biofeedback applications on the computing device.

Breathing rate can also be inferred from identification of the RSA pole. When the RSA pole is identified the phase angle $\theta_{RSA}$ of this pole relates to a measure of the current breathing rate of the subject via Equation 12 below:

$$f_b = \frac{\theta_{RSA}}{2\pi} f \qquad (12)$$

For a very weak RSA component in the original heart rate data the pole selection method may sometime select an incorrect pole and so this calculation for breathing rate may not be accurate. This is solved by thresholding the RSA pole energy. The threshold energy value, $E_{threshold}$, used in a preferred embodiment is 5.0 (corresponding to a pole magnitude of approximately 0.8). Below this threshold value the RSA component is assumed to be negligible and the breathing rate unknown. FIG. 5 also illustrates the RSA pole angle (identified as B) which at a sampling rate of 2 Hz corresponds to a breathing rate of 0.12 Hz (or 7 breaths per minute). This breathing rate can be displayed so that correlations between peaks in RSA component and current breathing rate can be identified. Alternatively the breathing rate that correlates with peak RSA can be stored and used later to set the frequency of looped audio or visual representation to help the user to more quickly synchronize their breathing in future sessions.

Figure 6:
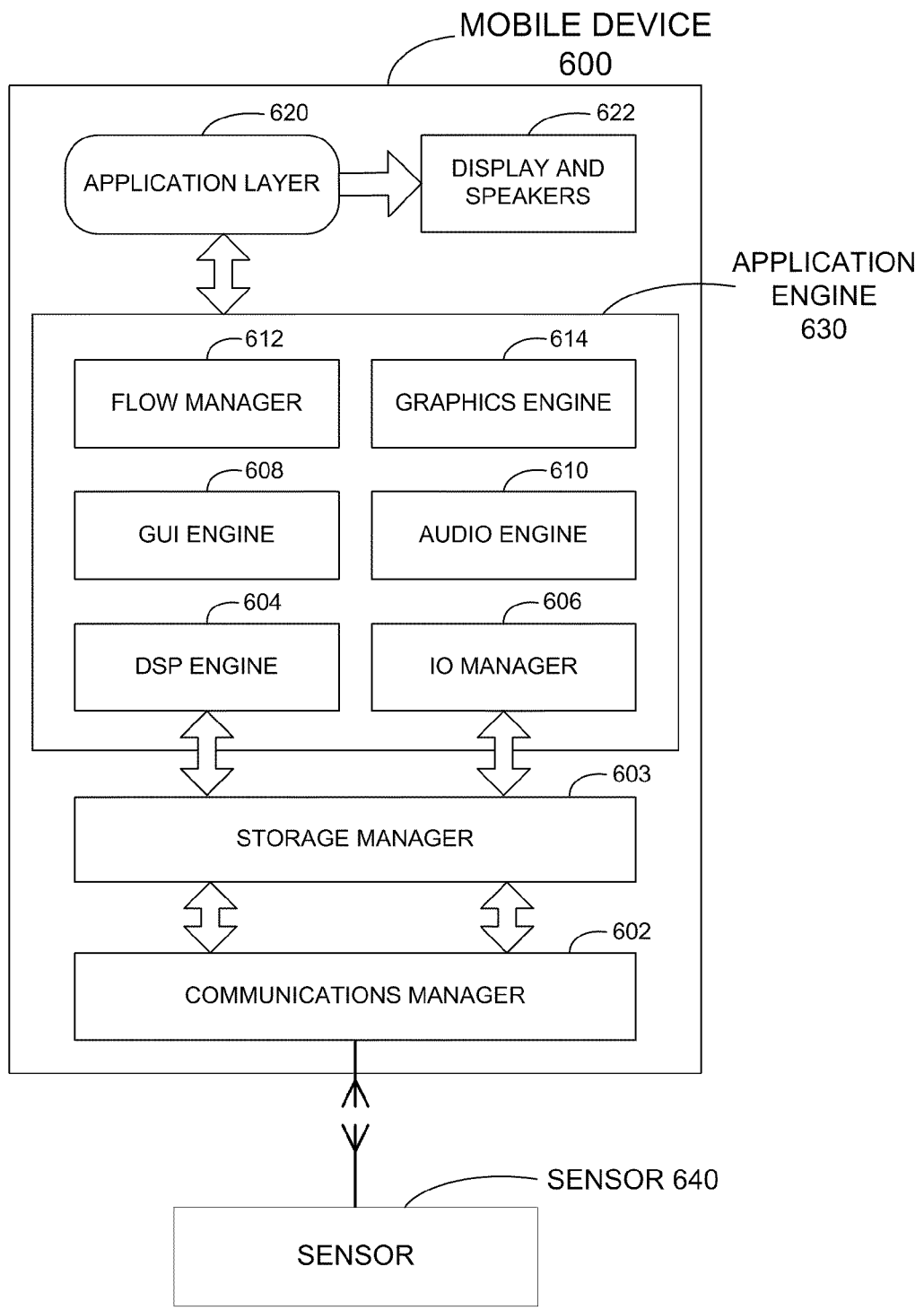
FIG. 6 illustrates an exemplary mobile device software architecture for implementing the subject invention.

FIG. 6 illustrates an exemplary mobile device software architecture for implementing method 400 as well as biometric applications that make use of the results of method 400. A mobile device 600 receives heart rate sensor data from a sensor 640. Mobile device 600 is an embodiment of computing device 308 and sensor 640 is an embodiment of sensor 304.

A communications manager 602 receives sensor data from sensor 640 and sends control signals as necessary to sensor 640 using a communications method such as BLUETOOTH communications. An application engine 630 provides a number of software modules or functions that support applications that run in an application layer 620. Applications in application layer 620 can display data and play sounds using a display and speakers 622.

A storage manager 603 stores received sensor data in a physical storage device. Typically the storage device is within mobile device 600 but it may also be connected via a network, USB connection or other physical or network connection.

Application engine 630 includes a digital signal processing (DSP) engine 604, an IO manager 606, a graphical user interface (GUI) engine 608, an audio engine 610, a flow manager 612 and a graphics engine 614.

DSP engine 604 computes RSA strength, and accumulated RSA, values. These values are used by a biometric application to affect audiovisual parameters. In a preferred embodiment, the method used to calculate RSA strength is that described with reference to FIG. 4.

IO manager 606 controls the flow of data from and to the application from external sources such as stored files.

Audio engine 610 manages all audio rendering of the application such as music and sound effects. In one embodiment of the invention this module includes the ability to modulate audio in real time base on instantaneous RSA strength.

Graphics engine 614 manages the rendering of application visuals to a screen. This includes rendering of graphic primitives such as lines and circles, rasterization of bitmaps and rendering of 3D scene graphs.

GUI engine 608 controls both user input event handling and rendering of onscreen user input elements such as buttons. This allows input events such as touchscreen or keypad events to be responded to within the application.

Flow manager 612 manages how the application is navigated by a user, i.e. the order in which application displays different canvases such as application settings or help screen to the user based on the users input.

These components of application engine 630 simplify the creation of RSA biofeedback applications such as those described below.

Biometric Applications that Use RSA Strength

In general the variation of RSA strength over time, referred to as $S_{RSA}(t)$ can be estimated There are several method known in the state of the art for estimating $S_{RSA}(t)$ from heart inter beat intervals. An example is measuring the peak to trough difference in heart rate over a 60 second interval. In a preferred embodiment, a method described below with reference to FIG. 4 is used. An accumulated measure of RSA strength, $A_{RSA}$, can serve as a metric of progress during a biofeedback session. Integrating $S_{RSA}(t)$ from time zero, the start of a biofeedback session, gives a measure of accumulated RSA, $A_{RSA}$. Biofeedback applications built around RSA can utilize both instantaneous RSA strength, $S_{RSA}(t)$, to give direct feedback of the level of their heart coherence as well as accumulated RSA, $A_{RSA}$, to give feedback of overall biofeedback session progress.

In a preferred embodiment the variation of RSA strength over time is modified by a weighting function before integration as in the following equation:

$$A_{RSA}(t) = \int_0^t w(S_{RSA}(t)) dt \qquad (13)$$

The weighting function w(x) allows the relationship between $A_{RSA}$ and $S_{RSA}$ to be adapted to specific requirements. As different applications may require differing metrics of progress this weighting allows the flexibility to achieve this. As an example, weighting allows progress to reverse as well as move forward by introducing negative weighting values (as $S_{RSA}$ is always positive and $A_{RSA}$ is always increasing without this negative weighting). In one embodiment, the function w(x) is represented as a step function with 5 levels as defined below:

$$w(x) = \begin{cases} -1 \forall \{x \le x_1\}, \\ 0 \forall \{x_1 < x \le x_2\}, \\ 1 \forall \{x_2 < x \le x_3\}, \\ 2 \forall \{x_3 < x \le x_4\}, \\ 3 \forall \{x < x_4\} \end{cases} \qquad (14)$$

where $x_1=0.5$, $x_2=1.0$, $x_3=2.5$, $x_4=4.0$.

The five level step function defined in Equation 14 above is implemented in the biometric application described below with reference to FIGS. 7A-D.

A target value of $A_{RSA}$ is specified to define the end point of a biofeedback session, i.e. a value which when reached signals that the session has been completed. $A_{RSA}$ is then used to provide feedback on progress during a session such as controlling an onscreen progress bar.

In another embodiment, when the target value $A_{RSA}$ is reached, the subject, i.e. the user of the biometric application, is awarded a designated number of points, henceforth referred to as relaxation points. Relaxation points are accumulated across a number of biofeedback sessions, enabling the subject to track progress over time.

Several biometric applications are described hereinbelow with reference to FIGS. 7A-D, 8, and 9. In each case the subject is represented by a virtual agent, i.e. a computer generated and maintained character that represents the subject. The movements made by and sounds emitted by the virtual agent are modulated by the biometric application and result in movements displayed to the subject by the virtual character or in relation to the virtual agent. In the exemplary biometric application described with reference to FIG. 7A-D the virtual agent is a plant. In an exemplary biometric application described with reference to FIG. 8 the virtual agent is a monk or spiritual guide.

Figure 7:
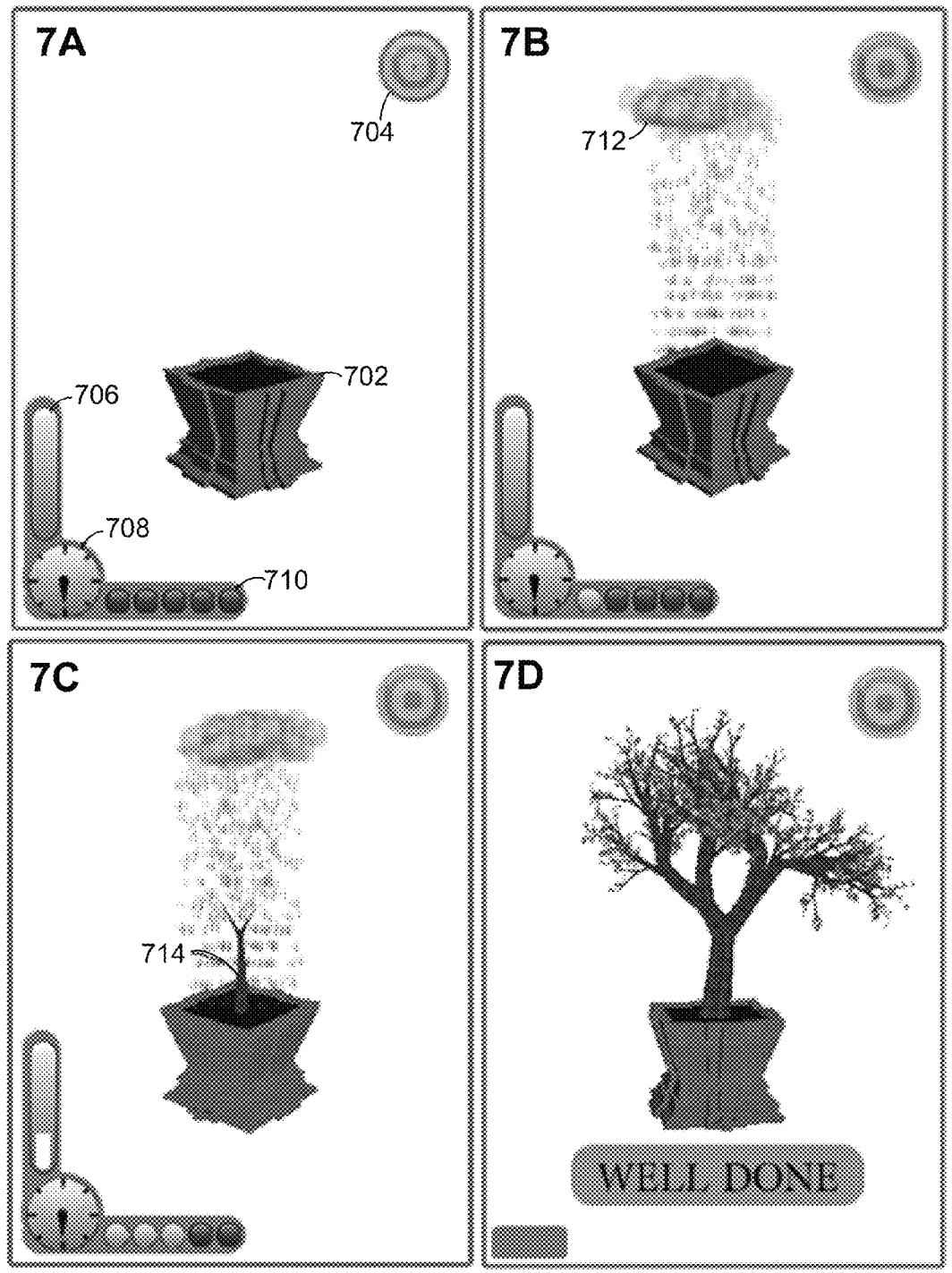
FIGS. 7A-D depicts several stages of a biofeedback application that maps the growth of a virtual plant to accumulated RSA during deep breathing.

A biofeedback application, described herein below with reference to FIGS. 7A-D, relates accumulated RSA to the growth of a virtual plant onscreen during a paced breathing biofeedback session. The growth of the plant is divided into a number of stages each one initiated when a target amount of accumulated RSA has been reached in the current biofeedback session. FIGS. 7A-D depict four stages of a plant's growth. FIG. 7A illustrates the initial state of the plant as an empty plant pot 702. The user's current RSA strength ($S_{RSA}$) is shown via the length of a bar 706. The overall accumulated RSA, $A_{RSA}$, progress indicator is shown by progress indicator 708 where the percentage progress is indicated by the angle of the dial. In another embodiment, a progress indicator is displayed as a water container in which water accumulates as accumulated RSA grows. The current growth stage is indicated via a stage indicator 710 which is consecutively highlighted as each stage is completed. In a preferred embodiment five stages are used to grow the plant from seed to a fully grown plant Once progress indicator 708 reaches 100% an animation plays in which water falls as rain onto the plant pot and a period of plant growth follows, as illustrated in FIG. 7B element 712. In another embodiment water falls from a watering can rather than from a cloud. Progress indicator 708 then resets to the start point and the process repeats through a number of stages in which the plant branches and grows. Early plant growth is depicted in FIG. 7C element 714. The completed state of the plant is illustrated in FIG. 7D along with a congratulatory message.

The growth of the plant can be pre animated and key framed so that each plant growth animation is always the same. In a preferred embodiment the plant growth animation is procedurally generated with several random inputs such as Perlin noise which allow each plant created to be individual and unique. This feature increases the chances that a user will regularly use the application as part of a stress control health regime.

Figure 8:
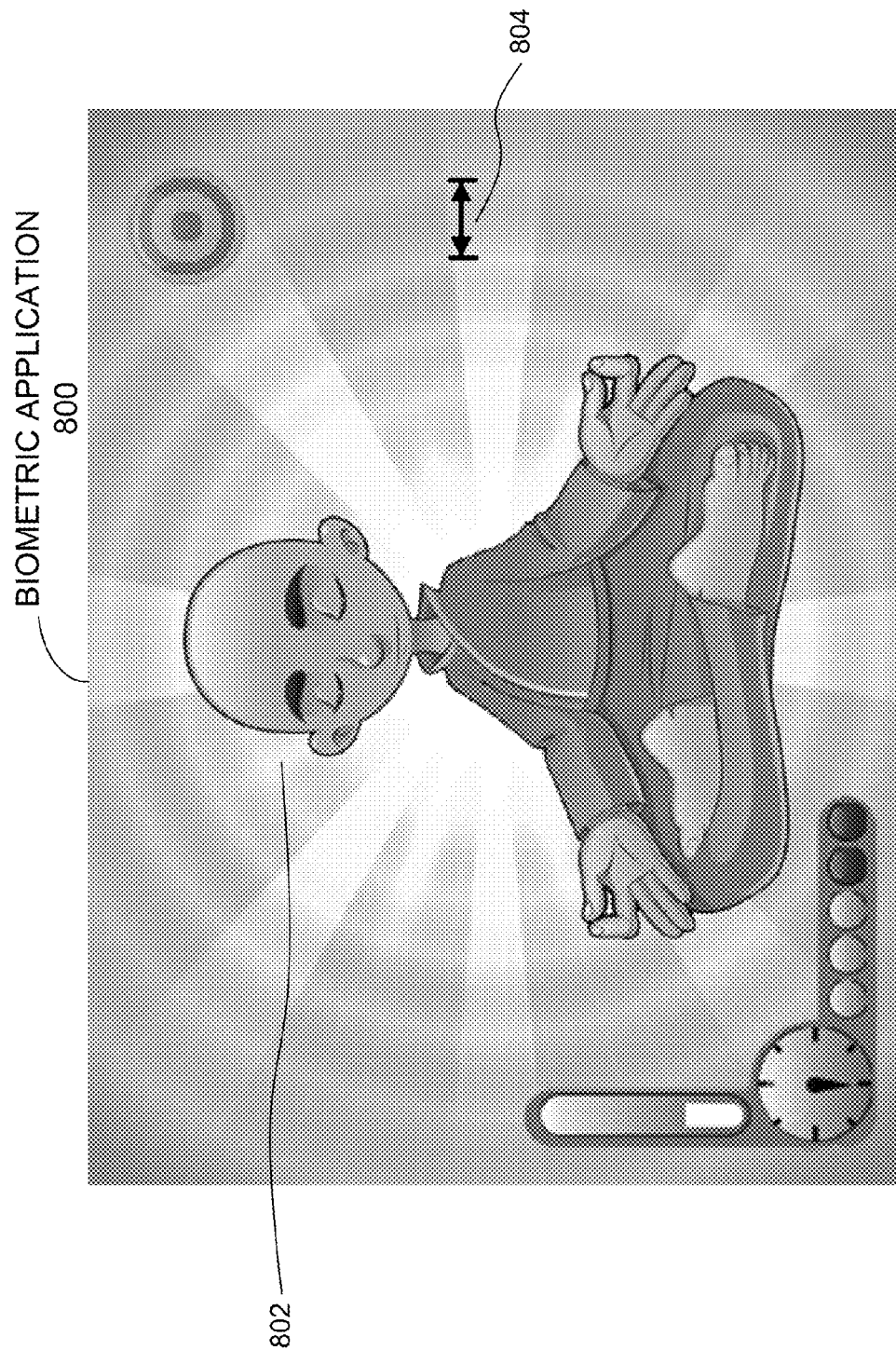
FIG. 8 illustrates one embodiment of a biofeedback application in which a virtual character is displayed to the subject and the behavior of the character is modulated by the subject's heartbeat RSA component strength.

FIG. 8 illustrates one embodiment of a biofeedback application in which a virtual agent is displayed to the subject and the behavior of the graphical or animated character is modulated by the subject's heartbeat RSA component strength. The onscreen graphical or animated character can have several modes of behavior such as sleeping, playing, reading or exercising. In biometric application 800, as illustrated in FIG. 8, the virtual agent is displayed as a meditating animated cartoon monk 802 seeking a higher spiritual state such as spiritual enlightenment, spiritual awakening, grace or nirvana, all referred to herein as spiritual enlightenment. In this embodiment, the monk must accumulate spiritual energy, i.e. accumulated RSA component, to reach the final state, spiritual enlightenment. The spiritual energy is accumulated over multiple RSA biofeedback sessions until the monk reaches the final state. The behavior of the monk correlates with the regularity of these sessions, the monk is happy and contented when his spiritual energy is being built up regularly but can be become tired and listless if he is neglected and the time between sessions grows too long. In a preferred embodiment each relaxation session shows the cartoon monk meditating beside a progress bar showing the accumulation of spiritual energy. One of the key aims of the application is to grow a bond between the subject and the playful monk and so provide a strong incentive to repeat RSA biofeedback sessions and so help the monk on his path to spiritual enlightenment, i.e. the final state.

In one embodiment, the subject, or user of the biometric application, can select a target amount of spiritual energy. For example, the subject can select from among a low, medium or high target amount. As a consequence, it will take a shorter or longer time, or number of sessions, for the subject to reach the target amount, or final state.

Biometric application 800 includes an animation that reflects the subjects rate of breathing, referred to as a breathing pacer animation. A breathing pacer animation typically reflects, visually, either the subject's actual breath rate, or a target breathing rate selected by the subject. In a preferred embodiment, a target breathing rate is selected by the user and an animated icon appears on screen that repeats at the targeted frequency during the RSA biofeedback session. In biometric application 800, the animated icon is a set of pulsing concentric circles that expand outward at the target breathing rate, i.e. distance moved between successive circles for at least one pair of concentric circles, as indicated by wavelength 804, is the inverse of the target breathing rate. In another embodiment the target breathing rate is signified by an icon that traces a circle around a center point. The use of a breathing pacer animation is not restricted to biometric application 800; it can be used in any biometric application based, at least in part, on RSA.

In another embodiment of a biofeedback application a virtual pet is displayed and the behavior of the virtual pet is modulated by the accumulated RSA, $A_{RSA}$. The behavior of the virtual pet is defined as an autonomous agent controlled via a number of internal drives such as tiredness, hunger or desire for knowledge. In this context a subject's $A_{RSA}$ can be mapped to one of these drives such as being used as a food or drink for the character. The virtual agent may be a virtual pet and $A_{RSA}$ may be used as a parameter the application uses to regulate the pet's health and happiness. The virtual pet will interact in a number of ways via an onscreen user interface such as play or go for walk but may only be fed based on $A_{RSA}$ i.e. based on the results of a biofeedback session with the user. This creates a context in which the virtual pet's overall health acts as a tracker for the regularity of biofeedback sessions and creates motivation by the user to keep to their routine of using the system and helping them stay relaxed.

Figure 9:
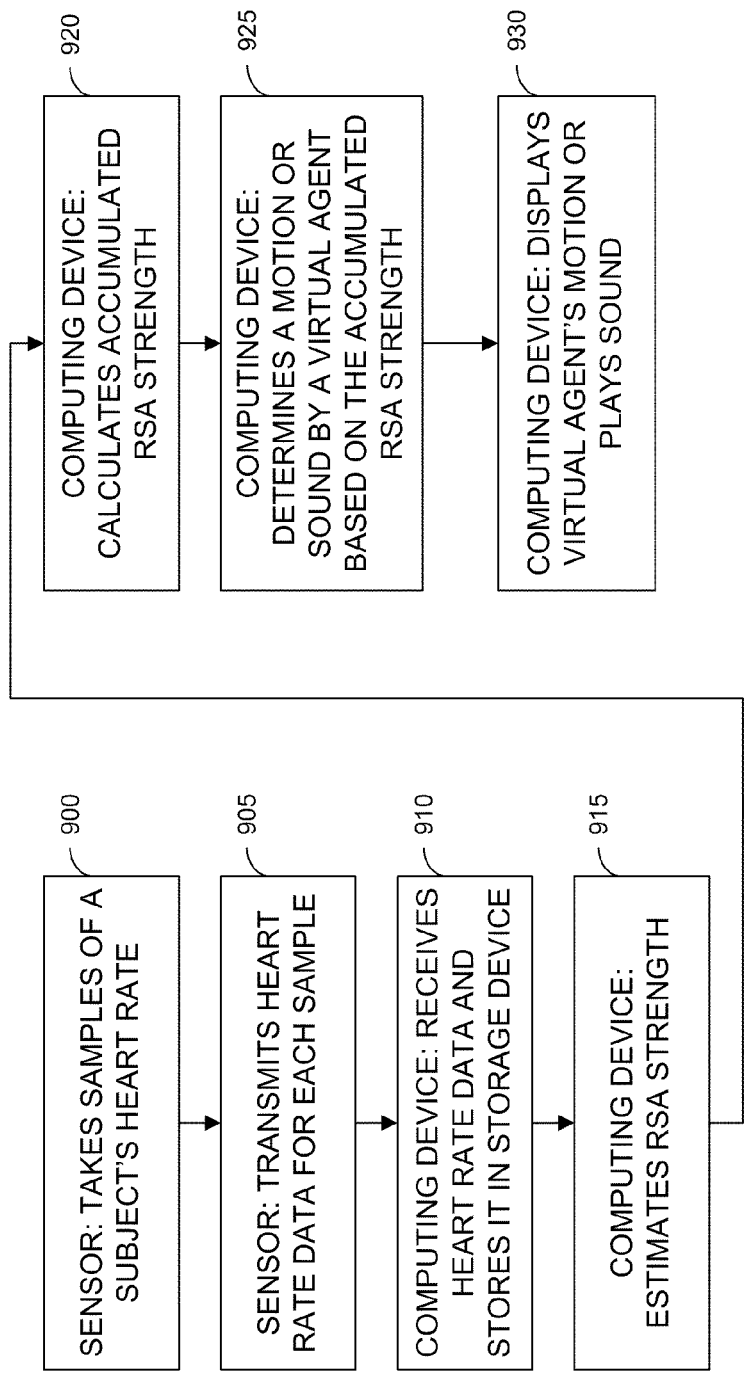
FIG. 9 is an overall method performed by the subject invention in which accumulated RSA is computed and is used to determine a graphical motion or sound made by a virtual agent that represents a human subject.

FIG. 9 is an overall method performed by the subject invention in which accumulated RSA is computed and is used to determine a motion or sound made by a virtual agent that represents a human subject. The virtual agent may be any character or object, for example, the virtual agent may be an animated person, a yogi, a martial artist, a superhero, a pet, a plant, a vehicle, an instrument, orchestra or band. At step 900 sensor 304 takes one or more samples of a subject's heart rate or heart activity. At step 905 the sensor, or a device to which it is attached, transmits heart rate data corresponding to the sample to computing device 308. At step 910 computing device 308 receives the heart rate data and stores it in a storage device within computing device 915. At step 915 computing device 308 calculates an estimate of RSA strength for the last received heart rate data sample. At step 920 computing device 308 calculates the accumulated RSA strength for an interval ending with the last received heart rate data sample. Typically, the beginning of the time interval is the start time for a biometric session when the subject most recently hooked up the sensor device and the sensor began transmitting heart rate data.

At step 925 a biometric application running on computing device 308 determines a motion to made by the virtual agent or a sound to be emitted by the virtual agent based on the most recent calculated value of the accumulated RSA strength. Finally, the biometric application running on computing device 308 displays the determined motion or plays the determined sound.

Multi-User Biometric Applications that Use RSA Strength

Figure 10:
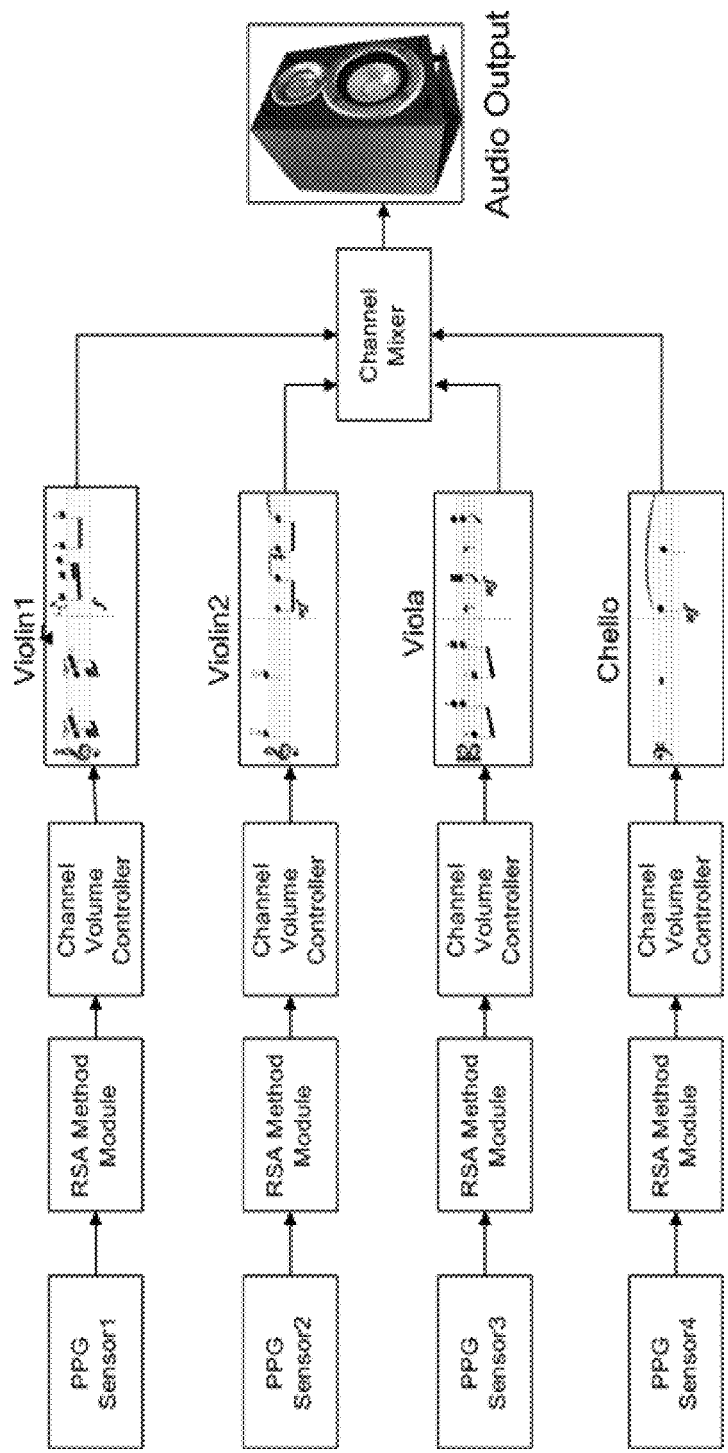
FIG. 10 is a simplified schematic of interactive virtual string quartet where accumulated RSA strength modulates individual channel volumes within a multiuser context.

RSA biofeedback methods may also be used within a multiuser application. One embodiment of such an application maps the $A_{RSA}$ from a number of users to the instruments of a virtual symphony orchestra, or virtual band. In one embodiment, each user's $A_{RSA}$ controls the volume of a single instrument in the virtual orchestra. As a user progresses in his/her biofeedback session his/her selected instrument is heard playing more distinctly, or louder. In combination, the users' efforts at maximizing their heart rate RSA components results in the orchestra sound growing in clarity and volume over time. Sections of the music piece being played may be repeated (in such a way as that no discontinuities are heard which is possible with judicious use of section boundary points and using overlapping volume fade in and fade out envelopes on the audio sections) if the overall group's progress has not reached target thresholds (the metric used may be an averaging of the groups individual $A_{RSA}$ or using the current minimum $A_{RSA}$ from the group) once a section has come to its end point. This allows the musical piece to "stretch" to fit the time taken by all the participants to progress to the finish point when all have reached their targeted $A_{RSA}$ values. The objective is to simultaneously reduce the anxiety levels within a group of individuals. FIG. 10 illustrates a simplified version including four users modulating the audio channels from a piece of music for a string quartet. One example of a use case for this application is in a classroom setting and is used before classes begin to help students relax and become more responsive to the lessons taught. This may be particularly useful where the students suffer from attention or hyperactivity disorders.

In reading the above description, persons skilled in the art will realize that there are many apparent variations that can be applied to the methods and systems described.

What is claimed is:

1. A computer-implemented method for calculating a Respiratory Sinus Arrhythmia (RSA) metric for use in biofeedback systems, comprising:

(a) sampling a subject's heart beat during a window of time by a sensor to obtain heart beat sensor data;

(b) transmitting, by the sensor, the heart beat sensor data corresponding to each sample during the window to a computing device;

(c) calculating, by the computing device, inter beat intervals from the heart beat sensor data;

(d) determining, by the computing device, an all-pole filter model that best fits the inter beat intervals;

(e) calculating, by the computing device, positions of filter model poles;

(f) identifying, by the computing device, the pole with the largest modulus within a pre-specified sector of a unit circle; and (g) calculating, by the computing device, an RSA metric, designated as $S_{RSA}$, calculated according to the equation, $$S_{RSA} = kE_w \left( \frac{1}{1 - |P_{RSA}|} \right)$$

wherein $P_{RSA}$ is the identified pole, $E_w$ is a total window energy, and k is a proportionality constant.

2. The method of claim 1 wherein the sensor is a transducer device selected from the group consisting of an electrocardiogram, a photoplethysmograph, a pressure sensor, and a microphone.

3. The method of claim 1 wherein the calculated inter beat intervals are resampled at a uniform rate.

4. The method of claim 1 further comprising de-meaning and de-trending, by the computing device, the samples in a window.

5. The method of claim 1 wherein the Burg method is used to calculate the best fit all-pole model filter coefficients.

6. The method of claim 1 wherein the pre-specified sector of the unit circle is defined by $$\frac{0.14\pi}{f_s} < \theta < \frac{0.66\pi}{f_s}$$

where $f_s$ is the sampling frequency.

7. The method of claim 1 wherein the pole with the largest modulus in the sector of interest is used to calculate the user's current breathing rate according to the equation, $$f_b = \frac{\theta_{RSA}}{2\pi} f_s$$

wherein $f_s$ is the sampling frequency, $\theta_{RSA}$ is the phase angle of the pole with the largest modulus and $f_b$ is the breathing frequency.

* * * * *